US012780848B2

(12) United States Patent
Kung et al.

(10) Patent No.: US 12,780,848 B2
(45) Date of Patent: Nov. 3, 2026

(54) [$^{18}$F]A1F LABELED PSMA TARGETING MOLECULAR PROBE AND PREPARATION METHOD THEREFOR

(71) Applicants: FIVE ELEVEN PHARMA, INC, Philadelphia, PA (US); BIOMOLECULAR PROBES BIOTECHNOLOGY (BEIJING) CO., LTD, Beijing (CN)

(72) Inventors: Hank F Kung, Philadelphia, PA (US); Zhihao Zha, Beijing (CN); Karl Ploessl, Philadelphia, PA (US); Seok Rye Choi, Philadelphia, PA (US); David Alexoff, Philadelphia, PA (US)

(73) Assignees: FIVE ELEVEN PHARMA, INC, Philadelphia, PA (US); BIOMOLECULAR PROBES BIOTECHNOLOGY (BEIJING) CO., LTD, Beijing (CN)

( * ) Notice: Subject to any disclaimer, the term of this patent is extended or adjusted under 35 U.S.C. 154(b) by 629 days.

(21) Appl. No.: 18/547,609

(22) PCT Filed: Mar. 17, 2021

(86) PCT No.: PCT/CN2021/078215
§ 371 (c)(1),
(2) Date: Aug. 23, 2023

(87) PCT Pub. No.: WO2022/193038
PCT Pub. Date: Sep. 22, 2022

(65) Prior Publication Data
US 2024/0158420 A1 May 16, 2024

(51) Int. Cl.
*C07F 5/06* (2006.01)
*G01N 33/574* (2006.01)
*G01N 33/68* (2006.01)

(52) U.S. Cl.
CPC ....... *C07F 5/069* (2013.01); *G01N 33/57434* (2013.01); *G01N 33/68* (2013.01)

(58) Field of Classification Search
CPC ............................ C09F 5/069; G01N 33/5743
See application file for complete search history.

(56) References Cited

U.S. PATENT DOCUMENTS

2013/0323171 A1 12/2013 Cheng et al.
2018/0250649 A1 9/2018 Alexoff et al.

FOREIGN PATENT DOCUMENTS

CN 108541302 A 9/2018

*Primary Examiner* — Paul V Ward
(74) *Attorney, Agent, or Firm* — NKL Law; Allen Xue

(57) ABSTRACT

A radiopharmaceuticals in clinical popularization is facilitated. By means of the biological characteristic of specifically targeting PSMA of the [$^{18}$F]AlF-P16-093, the labeled product has important potential clinical values in the aspects of early diagnosis, preoperative staging, treatment guidance, recurrence and metastasis focus detection of prostate cancer.

9 Claims, 4 Drawing Sheets

[68Ga]Ga-PSMA-11

[68Ga]Ga-P16-093

[$^{18}$F]A1F LABELED PSMA TARGETING MOLECULAR PROBE AND PREPARATION METHOD THEREFOR

TECHNICAL FIELD OF THE INVENTION

The present invention relates to a novel $^{18}$F labeled positron emission tomography (PET) molecular probe and a preparation method therefor, and particularly, to an [$^{18}$F]AlF labeled prostate specific membrane antigen (PSMA) targeting molecular probe and a preparation method therefor, and belongs to the technical field of radiolabeled compounds.

BACKGROUND

Positron emission tomography (PET) technology is a tip technology in the field of contemporary nuclear medicine, and also one of the state-of-the-art technical means for human beings to study life phenomena in the 21st century. It is a non-invasive, dynamic, and quantitative imaging technique that utilizes positron emitting drugs as molecular probes to evaluate physiological and biochemical changes in vivo, and has been widely used in the differential diagnosis and efficacy monitoring of diseases such as tumors, cardiovascular and cerebrovascular diseases, and neurological diseases. Wherein positron drugs are the “soul” of PET imaging, and their development and clinical translation are the key to the development of PET diagnostic techniques. Positron drugs refer to drugs labeled with positron emitting radioactive nuclides for clinical PET imaging.

Positron nuclides commonly used for PET imaging are $^{11}$C (half-life $T_{1/2}$=20.3 min), $^{18}$F (half-life $T_{1/2}$=109.8 min), $^{68}$Ga (half-life $T_{1/2}$=68.1 min), etc. $^{18}$F is currently the most widely used positron nuclide in clinical application, and has good nuclear chemistry properties. $^{18}$F labeled compound has been the focus of positron molecular probe development.

Prostate cancer is a urinary malignancy severely threatening the health of elderly men. With the development of population aging and popularization of prostate specific antigen (PSA) screening, incidence and mortality of prostate cancer in China grows year-by-year, and metastatic castration-resistant prostate cancer resulting from progressive prostate cancer is a leading cause of death. Early and accurate diagnosis of prostate cancer patients may allow for timely therapeutic interventions and personalized therapeutic regimens and thus reduce the mortality of prostate cancer.

Prostate-specific membrane antigen (PSMA) is a highly specific epithelial cell membrane antigen of the prostate, and it is an important diagnostic and therapeutic target for prostate cancer. PET imaging technology has the characteristics of precision and non-invasive. In recent years, various $^{68}$Ga-labeled PSMA-targeted PET imaging drugs have been reported in literature, represented by the unpatented $^{68}$Ga-PSMA-11. Hank F. Kung Laboratories developed a new generation of $^{68}$Ga-labeled radiopharmaceutical P16-093 based on existing PSMA targeting molecular probes, FIG. 1A illustrates the structure of $^{68}$Ga-PSMA-11; FIG. 1B illustrates the structure of $^{68}$Ga-P16-093.

$^{68}$Ga-P16-093 is coordinated with $^{68}Ga^{3+}$ (coordination constant~38.5) by using HBED-CC as a bifunctional linker, which labeling method is simple, high stability in vivo, has significant radioactive enrichment in tumor metastatic sites of patients and promising properties for imaging. Phase I/II clinical study data showed that the patient did not experience significant toxic side effects after injection of $^{68}$Ga-P16-093. Compared with $^{68}$Ga-PSMA-11, $^{68}$Ga-P16-093 showed a significant decrease in radiation uptake in urinary organs such as the bladder, and PET/CT imaging of the lesion site were more clear. As a novel PSMA targeting molecular probe, $^{68}$Ga-P16-093 can be used in the diagnosis and research of prostate cancer and kidney cancer. It has entered phase II clinical trial in United States (Clinical Trials. gov Identifier: NCT034444444).

Compared with $^{68}$Ga, $^{18}$F is currently the most widely used positron nuclide in clinical application and has good nuclear chemistry properties. $^{18}$F labeled compounds have always been the focus in the development of positron molecular probes.

To date, no researcher has conducted $^{18}$F labeling studies of P16-093. The inventor attempted to label P16-093 with $^{18}$F-AlF, and found that the labeling could be realized by adjusting the reaction conditions. The obtained $^{18}$F compound has superior biological properties and has the potential to be a new generation of PSMA positron molecular probes.

SUMMARY OF THE INVENTION

An object of the present invention is to overcome the deficiencies of the prior art and provide a [$^{18}$F]AlF labeled PSMA targeting molecular probe.

The aforementioned object of the present invention is realized through the following technical solutions:

A [$^{18}$F]AlF labeled PSMA targeting molecular probe, comprises a PSMA-targeting group and the bifunctional linker HBED-CC, wherein the probe has a formula as below:

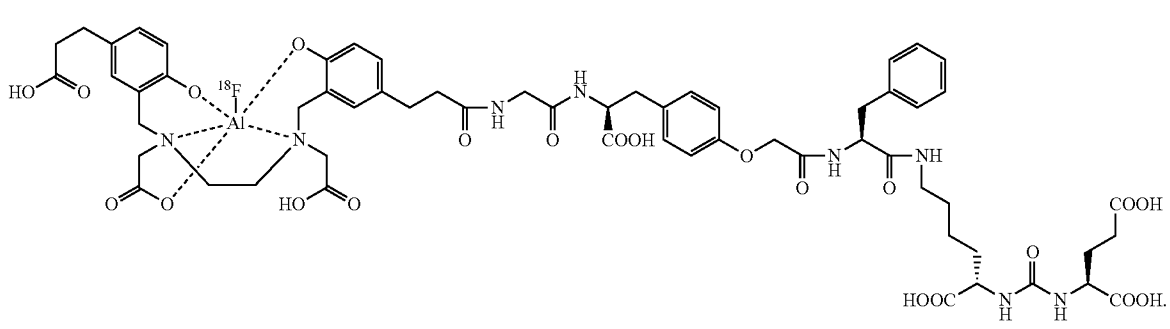

Another object of the present invention is to provide a preparation method for the aforementioned [$^{18}$F]AlF labeled PSMA targeting molecular probe.

The aforementioned object of the present invention is realized by the following technical solutions:

A preparation method for the aforementioned [$^{18}$F]AlF labeled PSMA targeting molecular probe, comprising the steps as below:

(1) P16-093 (PSMA-093) with the following structural formula was dissolved in sodium acetate buffer, and sodium hydroxide solution was added, adjusted the pH value to 4-6, and obtained a P16-093 sodium acetate solution;

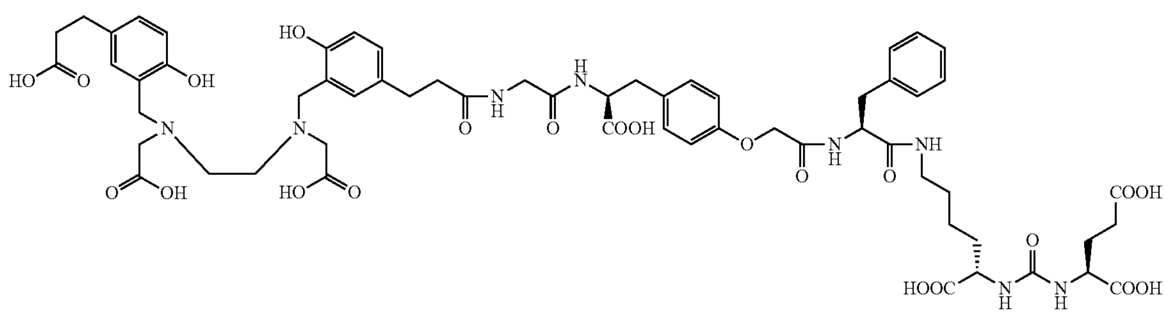 [SMILES: O=C(O)CCc1ccc(O)c(CN(CCN(CC(=O)O)Cc2cc(CCC(=O)NCC(=O)N[C@@H](Cc3ccc(OCC(=O)N[C@@H](Cc4ccccc4)C(=O)NCCCC[C@H](NC(=O)N[C@@H](CCC(=O)O)C(=O)O)C(=O)O)cc3)C(=O)O)ccc2O)CC(=O)O)c1]

(2) $^{18}F^-$ was prepared on a cyclotron by nuclear reaction $^{18}O(p,n)^{18}F$, which was then enriched on WATERS anion exchange column (sep-pak QMA), rinsed with deionized water to remove the metal impurity ions adsorbed on the sep-pak QMA column, and eluted with saline to obtain a saline solution;

(3) A sodium acetate buffer of $AlCl_3$ was added in a reaction vessel, and the saline solution prepared in step (2) was added and mixed evenly, and then the P16-093 sodium acetate solution prepared in step (1) and ethanol were added, the mixture was shaken evenly and reacted at 50-80° C. for 10-30 min, then cooling to ambient temperature to obtain a [$^{18}$F]AlF-P16-093 labeled reaction solution;

(4) The [$^{18}$F]AlF-P16-093 labeled reaction solution prepared in step (3) was purified to obtain the [$^{18}$F]AlF labeled PSMA targeting molecular probe.

Preferably, step (1) was as follows: 6 mg of P16-093 was dissolved in 2 mL of 0.05N sodium acetate buffer, and sodium hydroxide solution was added, adjusted the pH value to 5, and obtained a P16-093 sodium acetate solution at concentration of 3 mg/mL.

Preferably, step (2) was as follows: a sep-pak QMA column was pre-treated with 10 mL of 0.5M NaOAc solution and deionized water, and $^{18}F^-$ was prepared on a cyclotron by nuclear reaction $^{18}O(p,n)^{18}F$ and then enriched on the sep-pak QMA column, rinsed with deionized water to remove the metal impurity ions adsorbed on the sep-pak QMA column, and eluted with 0.2~1 mL of saline to obtain 1~2 GBq of a saline solution.

Preferably, step (3) was as follows: 4 μL of sodium acetate buffer of $AlCl_3$ was added in a reaction vessel, and 100 μL of the saline solution prepared in step (2) was added and mixed evenly, and then the P16-093 sodium acetate solution prepared in step (1) and 124 μL of ethanol were added. The mixture was shaken evenly and reacted at 50-80° C. for 10-30 min, then cooling to ambient temperature, the labeling yield was measured by high performance liquid chromatography (HPLC) to obtain a [$^{18}$F]AlF-P16-093 labeled reaction solution.

Preferably, step (4) was as follows: the [$^{18}$F]AlF-P16-093 labeled reaction solution prepared in step (3) was purified by solid phase extraction small column, the resulting product was diluted with saline to an ethanol content of less than 10%, its retention time and radiochemical purity were measured by HPLC, and its appearance was observed as a colorless clear transparent liquid to obtain a [$^{18}$F]AlF labeled PSMA targeting molecular probe.

Preferably, in step (3) and step (4), the first mobile phase was 0.1% aqueous solution of trifluoroacetic acid, the second mobile phase was acetonitrile, the gradient elution conditions were as follows: 0 min, 100% of the first mobile phase; 0~10 min, 100%~0% of first mobile phase; the flow rate of the mobile phase was 1 ml/min.

A further object of the present invention is to provide the use of the aforementioned [$^{18}$F]AlF labeled PSMA targeting molecular probe.

The aforementioned object of the present invention is realized by the following technical solutions:

Use of [$^{18}$F]AlF labeled PSMA targeting molecular probe in the diagnosis and detection of prostate cancer.

Preferably, the diagnosis and detection include early diagnosis, preoperative staging, treatment guidance, recurrence, and metastatic lesion detection.

Benefits:

1. Based on the molecular probe P16-093 which has entered Phase II clinical studies in the United States, the PSMA targeting molecular probe AlF-P16-093 is designed to be radiolabeled without affecting its biological activity, $^{18}$F is used as a radioactive nuclide, and the PSMA targeting molecular probe is labeled with the method of [$^{18}$F]AlF-HBED. The obtained [$^{18}$F]AlF labeled PSMA targeting molecular probe has excellent pharmacokinetic properties, high stability in vivo, has significant radioactive enrichment in tumor metastatic sites of patients, low bladder uptake, and has superior properties for imaging, which is more conducive to the detection of tumor lesions in pelvic location; moreover, the subject does not need to promote urination of bladder for imaging; in addition, the highest tumor uptake could be reached at 6 min post-injection, and the imaging time could be advanced to around 10 min post-injection (other $^{68}$Ga-labeled or $^{18}$F-labeled PSMA imaging agents need to be imaged 1~2 h post-injection), with clinically potential application value for local lesion detection and rapid imaging.
2. The aforementioned [$^{18}$F]AlF labeled PSMA targeting molecular probe, by means of the biological characteristic of specifically targeting PSMA, has important clinical potential values in early diagnosis, preoperative staging, treatment guidance, recurrence, and metastasis focus detection of prostate cancer.
3. The aforementioned [$^{18}$F]AlF labeled PSMA targeting molecular probe is radiolabeled by means of [$^{18}$F]AlF- HBED. The labeling method is simple, automatic synthesis is easy to realize, the labeling yield is high, HPLC purification is not required, which is important for radionuclides with shorter half-lives and is more conducive to commercial application of the radiolabeled compound in clinical promotion.

The subject matter of the present invention is further illustrated and described in connection with the example and the corresponding text and figures. There is no intent to limit the protection scope of the present invention.

DETAILED DESCRIPTION

Figure 1A:
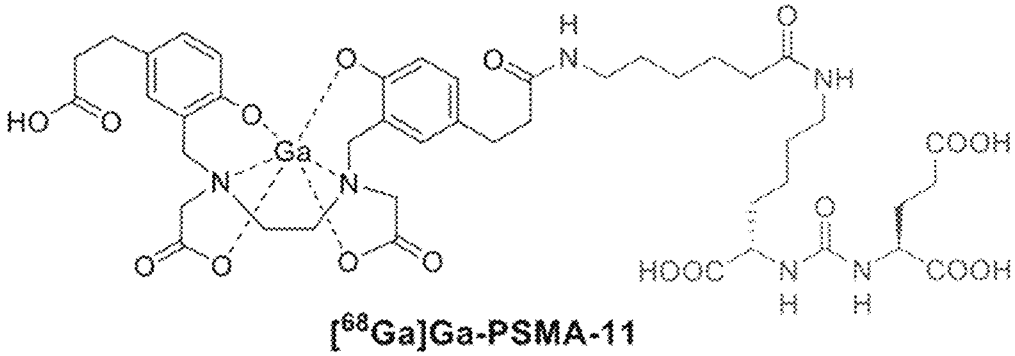
FIG. 1A illustrates the structure of $^{68}$Ga-PSMA-11.
Figure 1B:
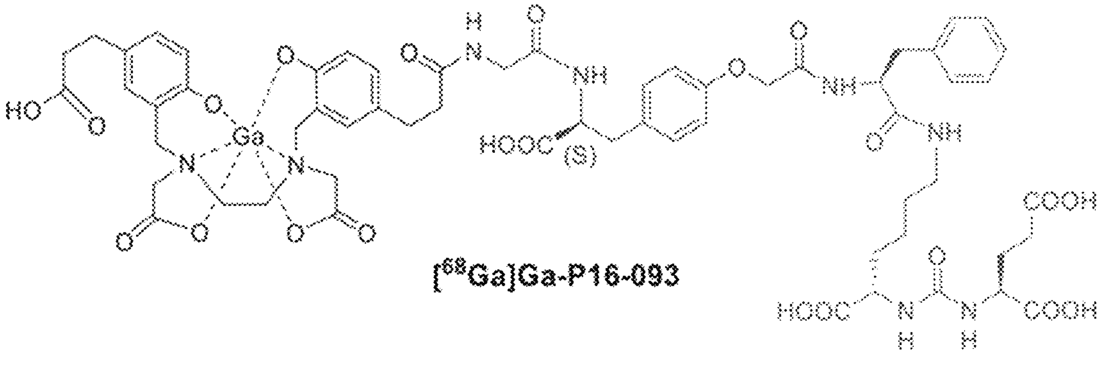
FIG. 1B illustrates the structure of $^{68}$Ga-P16-093.

Unless otherwise specified, the raw material and reagents mentioned in the examples of the present disclosure are the conventional ones that are commercially available, the test methods used are conventional, and the equipment and devices used are all conventional ones in this field.

A preparation method of the [$^{18}$F]AlF labeled PSMA targeting molecular probe, comprising the following steps:

(1) 100 mg of aluminum trifluoride and 5 mg of P16-093 (the structure formula was as follows) were dissolved in 2 mL of 0.05N sodium acetate solution buffer and 200 μL of ethanol, reacted at 80° C. for 30 min, cooled to ambient temperature, and purified by prep-HPLC to obtain the standard compound of AlF-P16-093, the purity was measured by high performance liquid chromatography (HPLC);

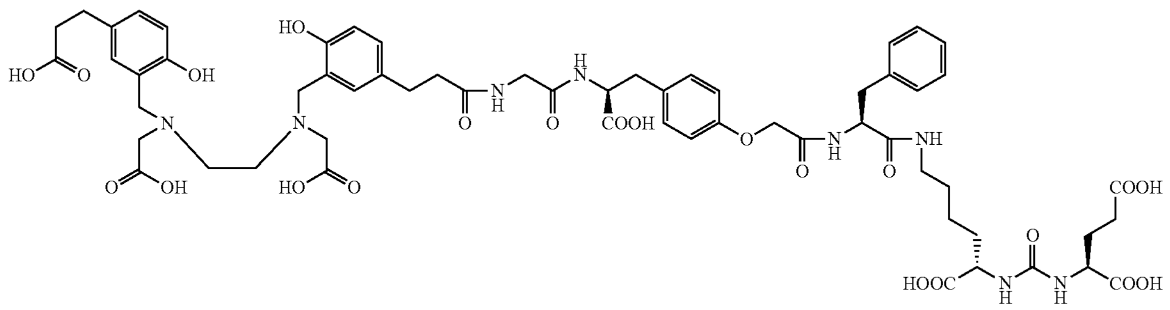 [SMILES: O=C(O)CCc1ccc(O)c(CN(CCN(CC(=O)O)Cc2cc(CCC(=O)NCC(=O)N[C@@H](Cc3ccc(OCC(=O)N[C@@H](Cc4ccccc4)C(=O)NCCCC[C@H](NC(=O)N[C@@H](CCC(=O)O)C(=O)O)C(=O)O)cc3)C(=O)O)ccc2O)CC(=O)O)c1]

The Structure of P16-093

(2) 6 mg of P16-093 (PSMA-093, supplied by Five Eleven Pharma, Inc., USA) was dissolved in 2 mL of 0.05N sodium acetate buffer, and sodium hydroxide solution was added, adjusted the pH value to 5 and obtained a P16-093 solution at concentration of 3 mg/mL;

(3) Sep-pak QMA column was pre-treated with 10 mL of 0.5M NaOAc solution and deionized water, and $^{18}F^-$ was prepared on a cyclotron by nuclear reaction $^{18}$O (p,n)$^{18}$F and then enriched on the sep-pak QMA column, rinsed with deionized water to remove the metal impurity ions adsorbed on the column, and eluted with 0.2~1 mL of saline to obtain 1~2 GBq of a saline solution;

(4) 4 μL of $AlCl_3$ (4 nmol) sodium acetate buffer was added to a reaction vessel, then 100 μL of saline solution prepared in step (3) was added and mixed evenly, and then P16-093 sodium acetate solution prepared in step (2) and 124 μL of ethanol were added, the mixture was shaken evenly and reacted at 50 to 80° C. for 10 to 30 min, after cooling to ambient temperature, the labeling yield was measured by HPLC to obtain a [$^{18}$F]AlF-P16-093 labeling solution;

(5) 6 mL of deionized water was added to the [$^{18}$F]AlF-P16-093 labeling reaction prepared in step (4) and mixed evenly, then purified by solid phase extraction small column, the resulting eluant was diluted with saline to the ethanol content of less than 10%, its appearance was observed as a colorless clear transparent liquid, and its retention time and radiochemical purity were measures by HPLC, and comparative analysis was performed with AlF-P16-093 standard, the consistent results indicating that a [$^{18}$F]AlF labeled PSMA targeting molecular probe was obtained, which has the following structure:

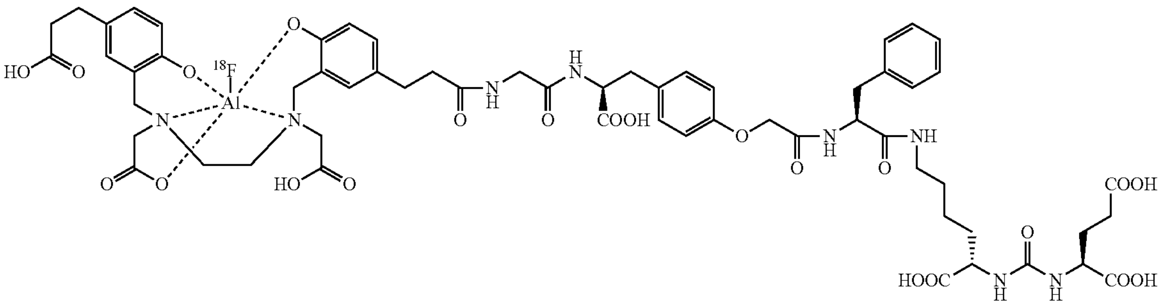

In high performance liquid chromatography (HPLC) aforementioned in step (1), step (4) and step (5), the first mobile phase was 0.1% aqueous solution of trifluoroacetic acid, the second mobile phase was acetonitrile, the gradient elution conditions were as follows: Omin, 100% of the first mobile phase; 0~10 min, 100%~0% of first mobile phase; the flow rate of the mobile phase was 1 ml/min.

Figure 2A:
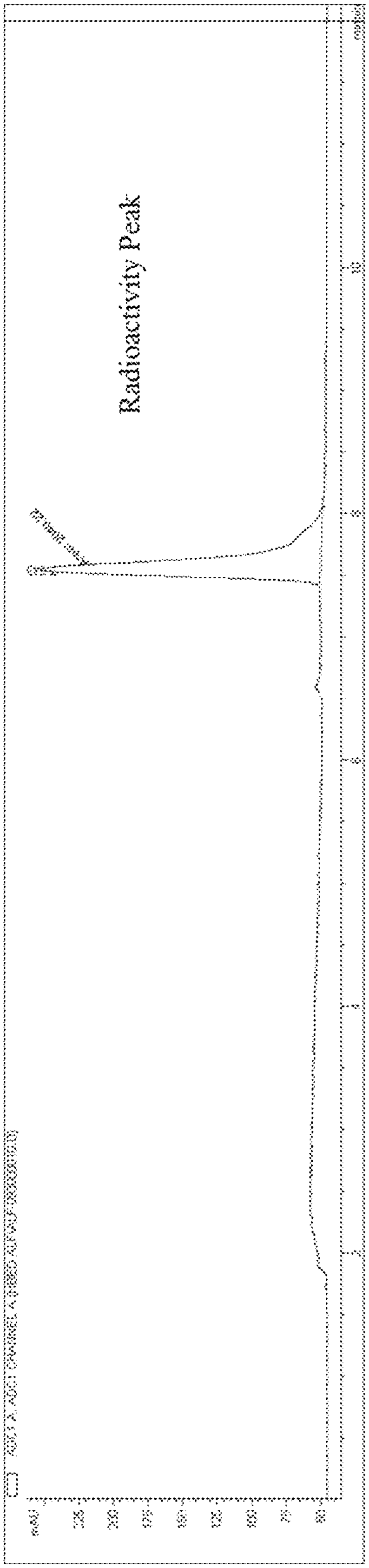
FIG. 2A illustrates the radioactivity peak chromatogram of [$^{18}$F]AlF-P16-093, with time in abscissa and radioactivity peak absorption intensity in ordinate.
Figure 2B:
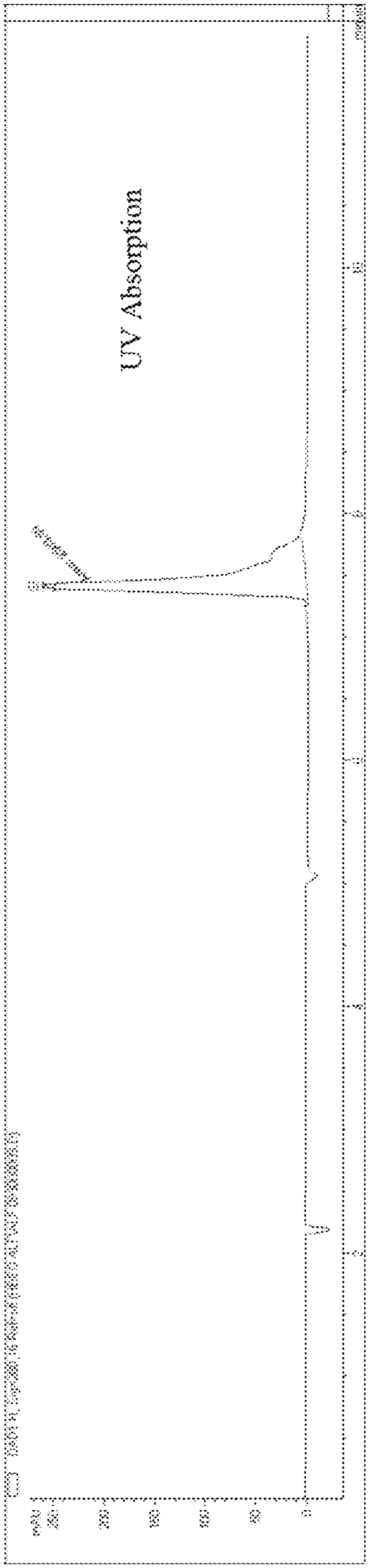
FIG. 2B illustrates the UV absorption spectrum of AlF-P16-093 standard, with time in abscissa and UV absorption intensity in ordinate.

FIG. 2A illustrates the radioactivity peak chromatogram of [$^{18}$F]AlF-P16-093, with time in abscissa and radioactivity peak absorption intensity in ordinate; FIG. 2B illustrates the UV absorption spectrum of AlF-P16-093 reference standard, with time in abscissa and UV absorption intensity in ordinate.

Application Example 1: In Vitro Autoradiography Experiments

Tumor mouse models of PC3-PIP (overexpressing of PSMA) and PC3 (no expressing of PSMA) were established, the PC3-PIP tumor, PC3 tumor and kidney tissue of the tumor mouse were sectioned at −20° C. with a thickness of 20 μm, the obtained sections were placed on a glass slide and dried in air for in vitro autoradiography studies. 1 mL of [$^{18}$F]AlF-P16-093 solution was overlaid on the tissue sections, incubated at room temperature for 60 minutes, and rinsed with PBS solution and deionized water for 3 minutes respectively, after drying, the tissue sections were covered with cling film and exposed overnight on a phosphorscreen, and then placed in a Cyclone Storage Phosphor System for imaging analysis.

Figures 3A, 3B, 3C:
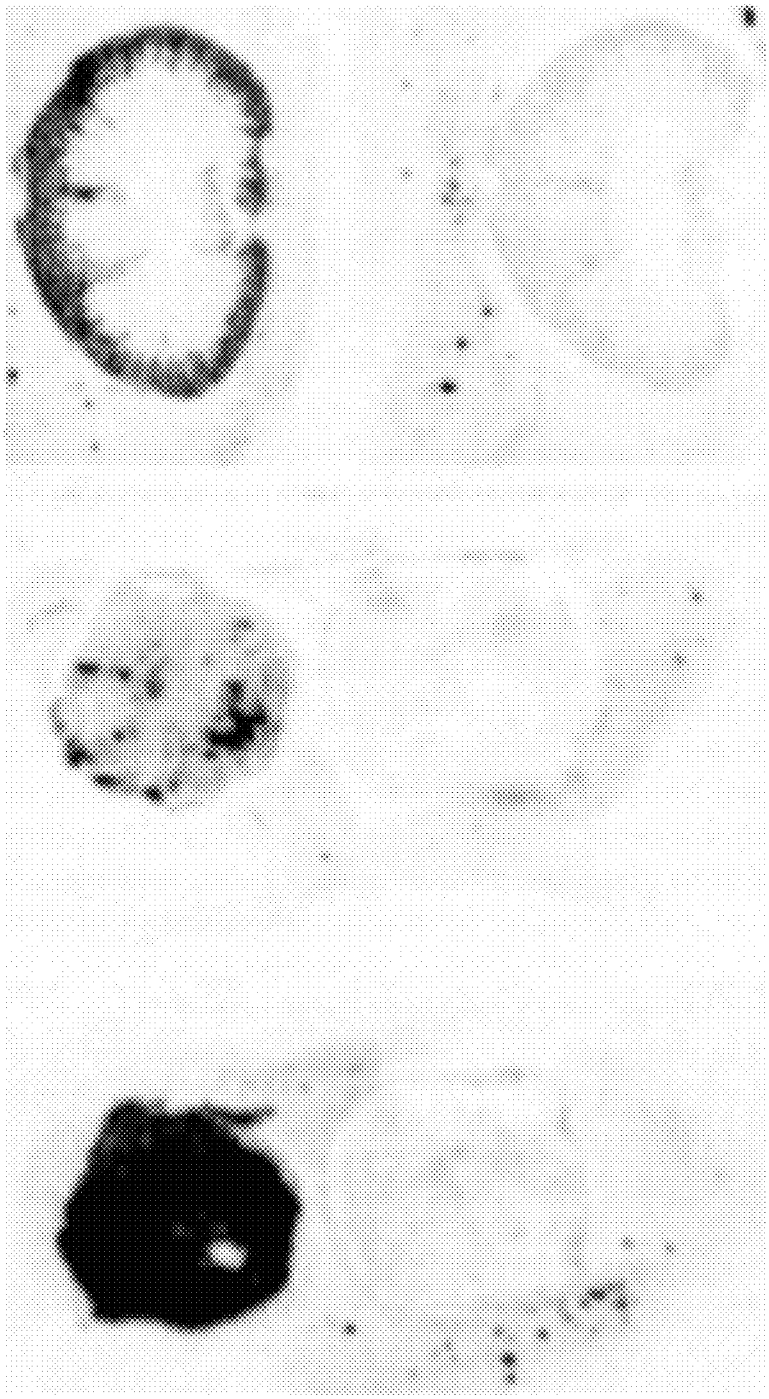
FIG. 3A illustrates the results of autoradiography study of [$^{18}$F]AlF-P16-093 in Example 1 of the present invention in PC3-PIP tumors, with the top half illustrates autoradiography without inhibitor and the bottom half illustrates autoradiography with inhibitor MIP-1095.
FIG. 3B illustrates the results of autoradiography study of [$^{18}$F]AlF-P16-093 in Example 1 of the present invention in PC3 tumors, with the top half illustrates autoradiography without inhibitor and the bottom half illustrates autoradiography with inhibitor MIP-1095.
FIG. 3C illustrates the results of autoradiography study of [$^{18}$F]AlF-P16-093 in Example 1 of the present invention in kidney tissues, the top half illustrates autoradiography without inhibitor and the bottom half illustrates autoradiography with inhibitor MIP-1095.

The results of in vitro autoradiography experiments are illustrated in FIG. 3A to FIG. 3C, FIG. 3A illustrates the results of autoradiography study of [$^{18}$F]AlF-P16-093 in Example 1 of the present invention in PC3-PIP tumors, with the top half illustrates autoradiography without inhibitor and the bottom half illustrates autoradiography with inhibitor MIP-1095; FIG. 3B illustrates the results of autoradiography study of [$^{18}$F]AlF-P16-093 in Example 1 of the present invention in PC3 tumors, with the top half illustrates autoradiography without inhibitor and the bottom half illustrates autoradiography with inhibitor MIP-1095; FIG. 3C illustrates the results of autoradiography study of [$^{18}$F]AlF-P16-093 in Example 1 of the present invention in kidney tissues, with the top half illustrates autoradiography without inhibitor and the bottom half illustrates autoradiography with inhibitor MIP-1095; [$^{18}$F]AlF-P16-093 was highly concentrated on PC3-PIP tumor and kidney sections (expressing PSMA), and no apparent uptake on PC3 tumor sections (not expressing PSMA).

Application Example 2: Cellular Uptake Experiments

PC3-PIP cells (expressing PSMA) and PC-3 cells (no expressing PSMA) were seeded separately in 12-well plates, RPMI 1640 culture fluid and fetal bovine serum FBS (v/v=9/1) were added, after incubation in a $CO_2$ incubator (5% of $CO_2$, 37° C.) for 24 hours, there were approximately $5\times10^5$ cells per well plate, the medium was moved, and washed twice with PBS, then PBS solution of [$^{18}$F]AlF-P16-093 or RPMI 1640 culture fluid was added, after incubation in a $CO_2$ incubator (5% of $CO_2$, 37° C.) for 0-120 minutes, the solution was removed, washed twice with 1 mL of cold PBS (without Ca2+ and Mg2+), the cells and cold PBS radioactive count were measured by a γ-Counter (radioactive counting instrument). Simultaneously, inhibition experiments were conducted, 10 μM MIP-1095 was added per well plate.

Figure 4:
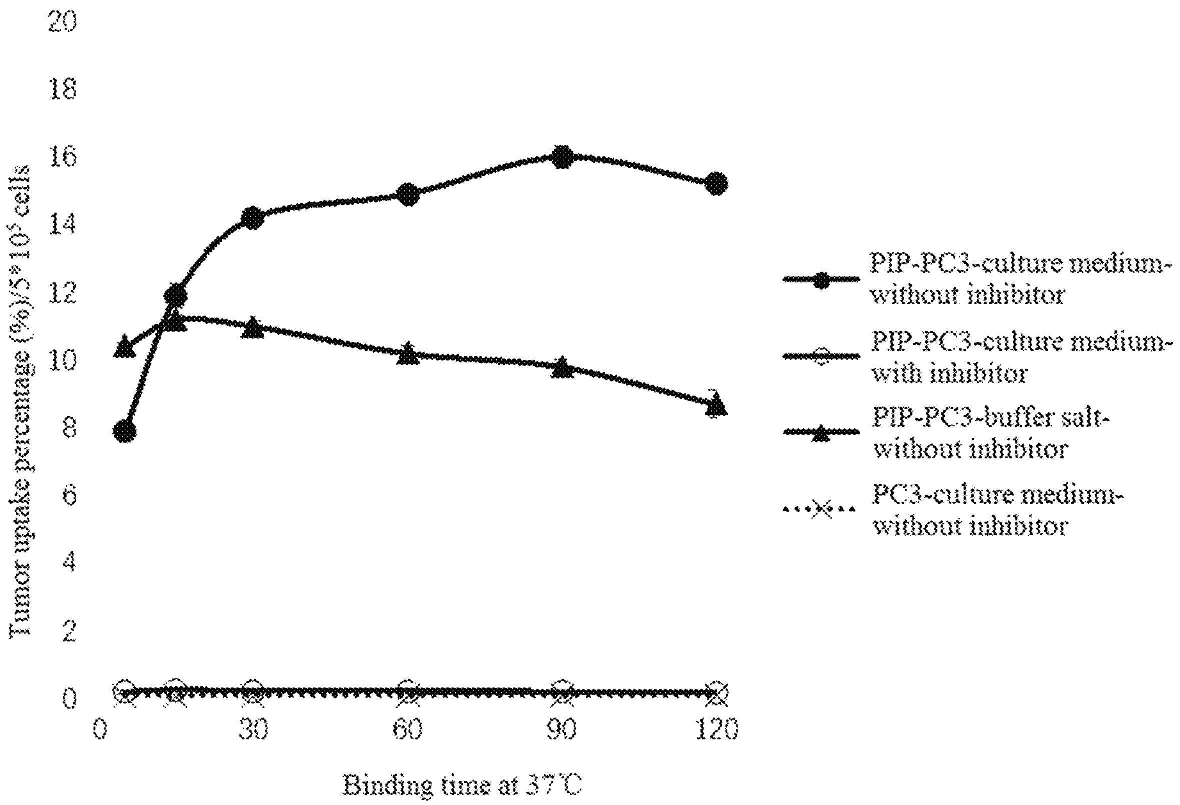
FIG. 4 illustrates the results of an uptake study of [$^{18}$F]AlF-P16-093 in Example 1 of the present invention in PC3-PIP cells and PC-3 cells.

The results of the cellular uptake studies of [$^{18}$F]AlF-P16-093 in Example 1 of the present invention in PC3-PIP cells and PC-3 cells are illustrated in FIG. 4: higher uptake of [$^{18}$F]AlF-P16-093 in PC3-PIP cells, and the uptake is gradually increased over time; low uptake (<0.1%) in PC-3 cells, which indicates that [$^{18}$F]AlF-P16-093 had specific uptake for PMSA.

Application Example 3: In Vivo Biodistribution Study In Tumor Mice

CD-I nude mice were implanted with PC3-PIP cells in the anterior left extremity axilla and PC3 cells in the anterior right extremity axilla and grown until tumors were 5-8 mm in diameter for biodistribution studies, by tail vein injection of 0.15 mL of [$^{18}$F]AlF-P16-093 saline (approximately 370 kBq), and tumor bearing nude mice were sacrificed anesthetically at different time points (30 min, 60 min and 120 min), dissected, tissue of interest weighed and radioactivity counted;

The results of in vivo biodistribution studies in tumor mice are illustrated in Table 1: [$^{18}$F]AlF-P16-093 in vivo biodistribution studies in tumor mice (% dose/g, avg±SD, n=4); it can be seen that [$^{18}$F]AlF-P16-093 uptake was higher in kidneys and PC3-PIP tumors of PSMA-high expressing, rising stepwise with time and reaching a maximum at 60 min; the uptake was lower in PC3 tumors which PSMA did not express; PC3-PIP tumor to muscle ratios were 17, 43 and 63 at 30 min, 60 min and 120 min respectively; PC3-PIP tumor to blood ratios were 11, 29 and 61 respectively.

TABLE 1

| | 30 m | 60 m | 120 m | 60 m Blocking* |
|---|---|---|---|---|
| Blood | 1.30 ± 0.24 | 0.68 ± 0.09 | 0.29 ± 0.02 | 0.50 ± 0.24 |
| Cardiac | 1.53 ± 0.43 | 0.82 ± 0.14 | 0.49 ± 0.08 | 0.35 ± 0.11 |
| Muscle | 0.89 ± 0.22 | 0.44 ± 0.03 | 0.29 ± 0.05 | 0.34 ± 0.19 |
| Lung | 2.75 ± 0.53 | 1.80 ± 0.22 | 1.23 ± 0.13 | 0.63 ± 0.21 |
| Kidney | 78.84 ± 13.64 | 98.57 ± 12.59 | 102.25 ± 16.97 | 2.11 ± 1.04 |
| Spleen | 7.08 ± 3.88 | 4.54 ± 1.52 | 2.52 ± 0.41 | 0.30 ± 0.19 |
| Liver | 1.69 ± 0.38 | 1.12 ± 0.15 | 0.71 ± 0.13 | 0.64 ± 0.28 |
| Bone | 2.92 ± 0.42 | 2.83 ± 0.49 | 4.20 ± 0.54 | 11.40 ± 1.61 |
| PIP-PC3 Tumors | 14.80 ± 4.82 | 18.84 ± 5.14 | 17.66 ± 3.34 | 2.15 ± 0.58 |
| PC3 Tumors | 1.87 ± 0.36 | 1.49 ± 0.03 | 1.11 ± 0.05 | 0.67 ± 0.27 |
| PIP-PC3/Blood | 11.26 ± 2.43 | 28.92 ± 12.11 | 60.96 ± 12.59 | 4.92 ± 2.59 |
| PIPPC3/Muscle | 16.68 ± 4.03 | 42.80 ± 13.13 | 63.39 ± 15.32 | 7.49 ± 3.83 |

In the present invention, $^{18}F$ is used as a radioactive labeled nuclide, and a PSMA targeting molecular probe is labeled by means of [$^{18}F$]AlF-HBED. The labeled [$^{18}F$]AlF-P16-093 has two advantages: firstly, the labeled method of [$^{18}F$]AlF-P16-093 is simple, evaporation and water removal are not required, automatic synthesis is easy to realize, the labeling yield is high, HPLC purification is not required, and commercial application of radiopharmaceuticals in clinical promotion is facilitated; and secondly, by means of the biological characteristic of specifically targeting PSMA of the [$^{18}F$]AlF-P16-093, the labeled product has important potential clinical values in early diagnosis, preoperative staging, treatment guidance, recurrence and metastasis focus detection of prostate cancer.

It is to be understood that the described examples herein are only some preferred examples of the present invention, there is no intent to limit the scope of implementation of the present invention. Equivalent changes and modifications made according to the patent scope and specification of the present invention should still fall within the scope of the present invention.

The invention claimed is:

1. A [$^{18}F$]AlF labeled PSMA targeting molecular probe, having a structural formula of:

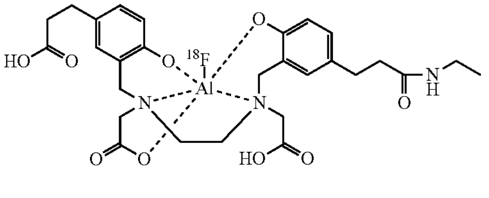

-continued

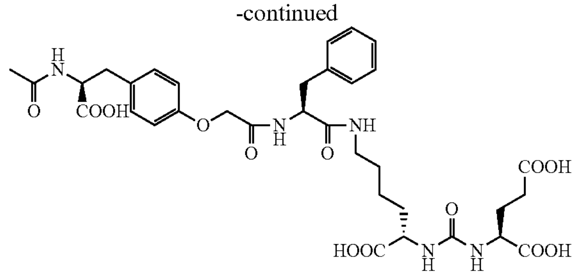

2. A preparation method of the [$^{18}F$]AlF labeled PSMA targeting molecular probe, comprising the following steps:

S1: dissolving P16-093 of the following structure formula in sodium acetate buffer, adding sodium hydroxide solution, adjusted the pH value to 4-6 and obtained a P16-093 sodium acetate solution;

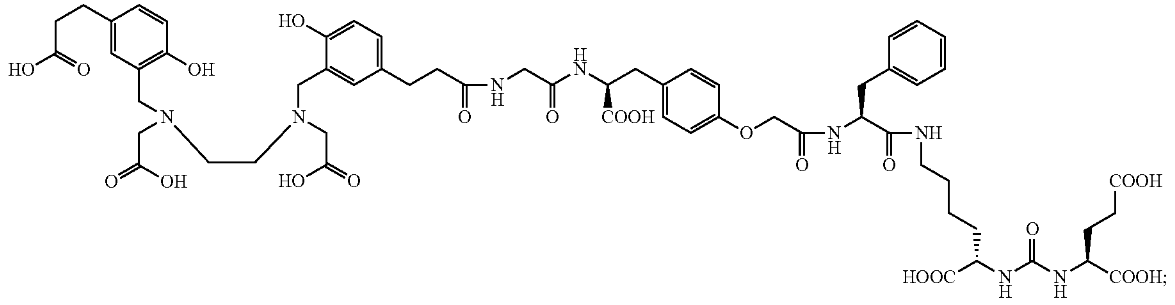

P16-093

S2: preparing $^{18}F^-$ is prepared on a cyclotron by nuclear reaction $^{18}O(p,n)^{18}F$, which is then enriched on anion exchange resin column, rinsing the anion exchange resin column with deionized water to remove metal impurity ions adsorbed thereon, and eluting the anion exchange resin column with saline to obtain a saline solution;

S3: mixing a sodium acetate buffer of $AlCl_3$ and the saline solution in a reactin vessel, and then adding the P16-093 sodium acetate solution prepared in step (1) and ethanol into the reaction vessel, shaking the mixture evenly and reacting at 50-80° C. for 10-30 min, then cooling the mixture to ambient temperature to obtain a [$^{18}F$]AlF-P16-093 labeled reaction solution; and S4: purifying the [$^{18}F$]AlF-P16-093 labeled reaction solution prepared to obtain the [$^{18}F$]AlF labeled PSMA targeting molecular probe.

3. The preparation method of the [$^{18}$F]AlF labeled PSMA targeting molecular probe according to claim 2, wherein S1 comprises dissolving 6 mg of P16-093 in 2 mL of 0.05N sodium acetate buffer, then adding sodium hydroxide solution, adjusting the pH value to 5; and obtaining a P16-093 solution at concentration of 3 mg/mL.

4. The preparation method of the [$^{18}$F]AlF labeled PSMA targeting molecular probe according to claim 3, wherein the anion exchange resin column is pretreated with 10 mL of 0.5M NaOAc solution and deionized water, and the elution is carried out using 0.2-1 mL saline to obtain 1-2 GBq of the saline solution.

5. The preparation method of the [$^{18}$F]AlF labeled PSMA targeting molecular probe according to claim 4, wherein S3 comprises adding 4 μL of the sodium acetate buffer of $AlCl_3$ to the reaction vessel, then adding 100 μL of the saline solution into the reaction vessel and mixing evenly, and then adding the P16-093 sodium acetate solution prepared and 124 μL of ethanol, shaking the mixture evenly and reacting at 50-80° C. for 10-30 min, cooling the mixture to ambient temperature, and measuring the labeling yield by HPLC to obtain the [$^{18}$F]AlF-P16-093 labeled reaction solution.

6. The preparation method of the [$^{18}$F]AlF labeled PSMA targeting molecular probe according to claim 5, wherein S4 comprises purifying the [$^{18}$F]AlF-P16-093 labeled reaction solution prepared by solid phase extraction small column, diluting a resulting product with saline to reduce ethanol content thereof to less than 10%, observing its appearance as a colorless clear transparent liquid and measuring its retention time and radiochemical purity by HPLC, and to obtain the [$^{18}$F]AlF labeled PSMA targeting molecular probe.

7. The preparation method of the [$^{18}$F]AlF labeled PSMA targeting molecular probe according to claim 6, wherein the HPLC has a first mobile phase that is 0.1% aqueous solution of trifluoroacetic acid, a second mobile phase is acetonitrile, and a gradient elution conditions includes 0 min, 100% of the first mobile phase; 0 to 10 min, 100% to 0% of first mobile phase; and a flow rate of the mobile phase was 1 ml/min.

8. A method for diagnosis and detection of prostate cancer, comprising administering the [$^{18}$F]AlF labeled PSMA targeting molecular probe according to claim 1 to a subject in need thereof.

9. The method according to claim 8, wherein the diagnosis and detection of prostate cancer comprise early diagnosis, preoperative staging, treatment guidance, recurrence or metastatic lesion detection.

* * * * *